(12) United States Patent
Deng et al.

(10) Patent No.: US 6,601,406 B1
(45) Date of Patent: Aug. 5, 2003

(54) METHODS AND APPARATUS FOR HIGH PROPANE RECOVERY

(75) Inventors: Eh Deng, Irvine, CA (US); John Mak, Santa Ana, CA (US); Richard B. Nielsen, Laguna Niguel, CA (US)

(73) Assignee: Fluor Corporation, Aliso Viejo, CA (US)

( * ) Notice: Subject to any disclaimer, the term of this patent is extended or adjusted under 35 U.S.C. 154(b) by 0 days.

(21) Appl. No.: 10/088,839

(22) PCT Filed: Oct. 20, 2000

(86) PCT No.: PCT/US00/41428

§ 371 (c)(1),
(2), (4) Date: Jun. 19, 2002

(87) PCT Pub. No.: WO01/34726

PCT Pub. Date: May 17, 2001

Related U.S. Application Data

(60) Provisional application No. 60/161,297, filed on Oct. 21, 1999.

(51) Int. Cl.[7] .................................................. F25J 3/00
(52) U.S. Cl. ........................................... 62/621; 62/631
(58) Field of Search ........................... 62/621, 630, 631

(56) References Cited

U.S. PATENT DOCUMENTS

| | | | |
|---|---|---|---|
| 2,236,965 A | 4/1941 | Babcock | 62/122 |
| 3,362,175 A | 1/1968 | Burns et al. | 62/38 |
| 4,370,156 A | 1/1983 | Goddin, Jr. et al. | 62/17 |

*Primary Examiner*—Ronald Capossela
(74) *Attorney, Agent, or Firm*—Rutan & Tucker, LLP

(57) ABSTRACT

Methods and configurations for improved propane recovery plant employ an absorber column, and a deethanizer column with an overhead condenser that produces a reflux condensate. The reflux condensate is recycled to both the absorber column and the deethanizer column, and a third recycling loop feeds propane from the absorber column into the deethanizer column in a gaseous form. The overhead condenser employs cold reject gas from the absorber and/or propane as a refrigerant, and preferred deethanizer columns include an integral water removal contactor.

20 Claims, 1 Drawing Sheet

METHODS AND APPARATUS FOR HIGH PROPANE RECOVERY

This application claims the benefit of U.S. provisional application No. 60/161,297, filed Oct. 21, 1999, which is incorporated herein by reference in its entirety.

FIELD OF THE INVENTION

The field of the invention is separation of hydrocarbon gas.

BACKGROUND OF THE INVENTION

Propane is a valuable component in industrial gases and various processes are known in the art, including processes based on cooling and refrigeration of gas, oil absorption and refrigerated oil absorption, and especially cryogenic expansion processes. However, all or almost all of them suffer from one or more disadvantages.

For example, in U.S. Pat. No. 4,157,904 to Campbell (Jun. 12, 1979), a process for propane recovery employs a cooled feed gas stream that is partially condensed, subsequently expanded to a lower pressure, and then separated in a distillation column. The separation is improved by combining the condensed liquid with a stream having a lower bubble point with cooling of one or both streams prior to expansion. Campbell's recovery process advantageously increases the overall energy efficiency, however, requires at least in some configurations additional material translating to increased plant construction costs.

In another example, U.S. Pat. No. 4,854,955 to Campbell et al. (Aug. 8, 1989), a process for recovery of propane includes dividing a hydrocarbon stream into first and second streams and subsequent condensation and expansion of the first stream, which is then heat exchanged with a column reject from the distillation column. A portion of the partially condensed column reject is refluxed to the distillation column. Although Campbell's configuration tends to increase the recovery of propane, the inlet feed gas is typically restricted to dried feed gas.

In a further example, U.S. Pat. No. 5,890,378 to Rambo et al. (Apr. 6, 1999), a configuration for improved propane recovery is described in which much of the equipment required for providing reflux for the absorption section is eliminated while maintaining relatively high propane yields. Although Rambo's configuration generally reduces equipment related costs to at least some degree, the treatment of a vapor phase feed gas stream and a wet liquid from the feed gas typically require separate processes involving significant amounts of equipment.

Although there are various processes known in the art, all or almost all of them suffer from one or more disadvantages. Therefore, there is still a need to provide improved methods and apparatus for high propane recovery.

SUMMARY OF THE INVENTION

The present invention is directed to methods and apparatus for improved propane recovery. In particular, a propane recovery plant has an absorber column.that receives a feed gas, and that produces a cold reject vapor and a product fluid. A second column receives at least part of the product fluid in a gas form, and the second column is further fluidly coupled to a condenser that forms a reflux condensate by using at least in part the cold reject vapor as a refrigerant. It is generally contemplated that a first portion of the reflux condensate is recycled into the second column, and that a second portion of the reflux condensate is fed into the absorber column.

In one aspect of the inventive subject matter, the second column comprises a deethanizer column, which may further include an integral water removal contactor, especially when the deethanizer further receives a wet liquid feed gas. Where an integral water removal contactor is utilized, preferred scrubbing agents include triethylene glycol.

In another aspect of the inventive subject matter, the condenser is preferably an integral overhead condenser that may employ propane as a refrigerant. While contemplated methods and configurations are generally contemplated to improve propane recovery, it is particularly contemplated that the recovery is up to 99 mol %, and where propane is employed as a refrigerant it is contemplated that the recovery is up to 99 mol %.

In a further aspect of the inventive subject matter, a feed gas separation element receives a wet process gas, and produces a wet gaseous feed gas and a wet fluid feed gas. A deethanizer column receives the wet fluid feed gas, wherein the deethanizer column comprises an integral water removal contactor, and wherein the deethanizer column further comprises an integral overhead condenser that forms a reflux condensate, of which a first portion is recycled into the deethanizer column and of which a second portion is fed into an absorber column.

In a still further aspect of the inventive subject matter, a method of improving the recovery of propane from a feed gas has a step of providing an absorber column, and a deethanizer column with an overhead condenser that utilizes at least in part a cold reject vapor from the absorber column as a refrigerant, wherein the overhead condenser produces a reflux fluid. In a further step, a first recycling loop is formed in which a first portion of the reflux fluid is recycled into the deethanizer column, and in another step a second recycling loop is formed in which a second portion of the reflux fluid is fed into the absorber column. In yet another step, a third recycling loop is formed in which a product fluid from the absorber is fed into the deethanizer column in a gaseous form.

Various objects, features, aspects and advantages of the present invention will become more apparent from the following detailed description of preferred embodiments of the invention, along with the accompanying drawing.

DETAILED DESCRIPTION

Figure 1:
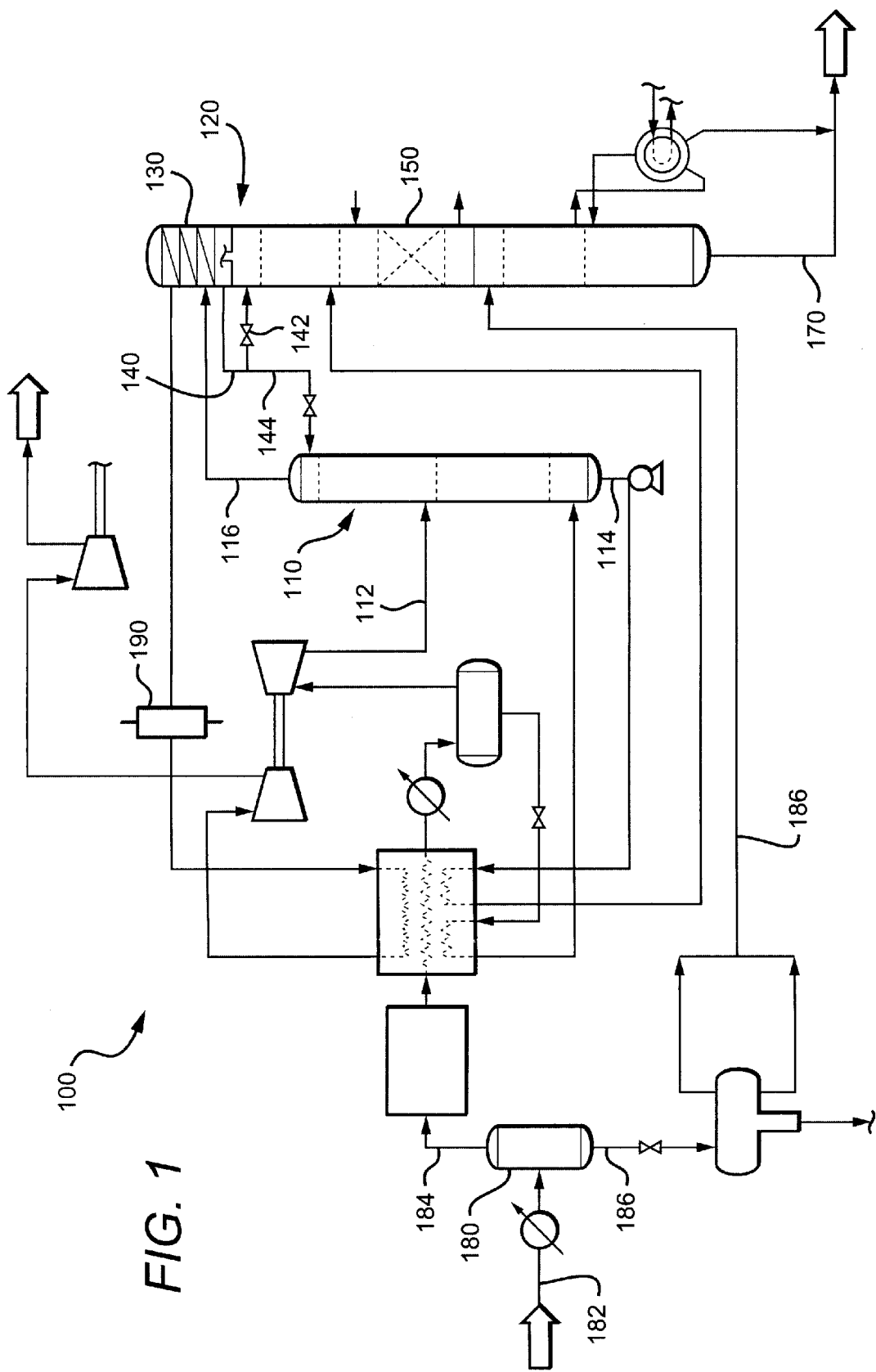
FIG. 1 is a schematic view of an improved propane recovery plant according to the inventive subject matter.

In FIG. 1, an improved propane recovery plant 100 has an absorber column 110 and a second column 120. The absorber column 110 receives absorber feed gas 112 and produces cold reject vapor 116 at the top end and a product fluid 114 at the bottom end. The cold reject vapor 116 is employed as a refrigerant in the integral overhead condenser 130, which produces a reflux condensate 140. A first portion 142 of the reflux condensate 140 is recycled back into the second column, while a second portion 144 of the reflux condensate 140 is fed into the absorber column 110. Purified product fluid 170 is extracted from the second column on the bottom end. An optional propane refrigeration unit 190 cools the refrigerant for the integral overhead condenser 130.

A gas separation element 180 receives wet process gas 182 and produces wet gaseous feed gas 184 and wet liquid feed gas 186, which is fed into the second column (e.g., a deethanizer) at a point below the integral water removal contactor 150.

In a preferred aspect of the inventive subject matter, the absorber column 110 is a conventional distillation column with one or more trays, packed beds or any reasonable combination thereof. Contemplated absorber columns 110 have a capacity of about 600 MMscfd at a height of approximately 90 ft and a diameter of about 10 feet, allowing a gas throughput of approximately 600 MMscfd. Although not limiting to the inventive subject matter, contemplated absorber columns may comprise an upper and a lower section. The upper section generally acts as a separator in which vapor is separated from the corresponding liquid portion, and in which desirable vapors not absorbed in the lower section will combine with the liquid portion separated in the upper section. The lower section generally acts as an stripper onto which the ethane or other desirable gaseous component are removed.

It should be appreciated, however, that various alternative absorber columns are also appropriate, and alternative absorber columns include configurations that contain multiple sections and feed points. Similarly, the capacity of the absorber need not be limited to a particular volume at a specific height and/or diameter. Consequently, suitable alternative absorbers may have a capacity between 400 MMscfd and 600 MMscfd, and higher, or between 100 MMscfd and 400 MMscfd, and less. However, it should be especially recognized that the absorber column is a separate structure from the second column (e.g., deethanizer column). The term "separate structure" as used herein means that the absorber column is not stacked on top of the second column, or vice versa. Viewed from another angle, it is contemplated that the improved propane recovery process may be performed in a "cold" section (i.e., a section at a temperature between about −50° C. and −90° C.) and a "warm" section (i.e., a section at a temperature of higher than about −50° C.). It should be especially recognized that separation of the improved propane recovery process in a cold section and a warm section permits significant reduction in material costs, since only the cold section requires the use of stainless steel, and the deethanizer or second column may be fabricated from low temperature carbon steel.

It is further contemplated that suitable absorbers receive an absorber feed gas 112 (infra), and that the absorber further produces a product fluid 114, typically liquid propane, or other desirable compound that contains impurities to at least some degree. To increase the recovery of the propane or other desirable compound, it is contemplated that the product fluid 114 is heated (e.g., in a heat exchanger) to convert the product fluid into the gas form, and that the product fluid in the gas form is subsequently introduced into the second column (e.g., deethanizer column). With respect to the point of introduction, it is contemplated that various points are suitable, however, it is preferred that the point of introduction is above an optional integral water removal contactor, but below the point at which the first portion of the reflux condensate enters the second column.

With respect to the second column, it is preferred that the second column comprises a deethanizer column. There are many deethanizer columns known in the art, and all of the known deethanizer columns are contemplated suitable for use in conjunction with the teachings presented herein. For example, an appropriate deethanizer column may comprise a conventional distillation column with one or more trays, packed beds or any reasonable combination thereof.

Contemplated deethanizer columns 120 have a capacity of about 100 MMscfd at a height of approximately 100 feet and a diameter of about 10 ft, allowing a gas throughput of approximately 100 MMscd. It is further contemplated that contemplated deethanizer columns may comprise an upper and a lower section with the upper section generally acting as a separator in which vapor is separated from the corresponding liquid portion, and in which vapors not absorbed in the lower section will combine with the liquids separated in the upper section. The lower section generally acts as an stripper onto which the ethane or other undesirable gaseous component is removed. It should further be appreciated that suitable deethanizer columns also include a reboiler to provide the stripping vapors that strip the liquid product from the undesirable components. Contemplated second columns produce a purified product fluid, and typically comprise a bottom outlet for the purified product fluid. Contemplated purified product fluids include, for example, liquid gas predominantly comprising propane and higher hydrocarbons. The term "higher hydrocarbons" as used herein refers to volatile (at room temperature) carbohydrates with four to six carbon atoms.

It is particularly preferred, however, that the deethanizer column 120 is fluidly coupled to a condenser 130, preferably an integrated overhead condenser. The term "integrated" device as used herein means that the device is disposed within a column. It is further contemplated that the condenser 130 employs a refrigerant, and it is particularly contemplated that the refrigerant comprises the cold reject vapor 116 from the absorber, propane, or any reasonable combination thereof However, it should also be appreciated that while preferred condensers are integrated overhead condensers, alternative condensers may also be disposed outside of the deethanizer column or on any other suitable position so long as contemplated condensers provide at least one reflux condensate from the deethanizer.

Contemplated condenser 130 produces a reflux condensate 140 from the reject vapors in the deethanizer, and the reflux condensate 140 is split in at least a first portion 142 and a second portion 144. It is generally preferred that the first portion 142 of the reflux condensate is recycled into a lower portion of the deethanizer, and that the second portion 144 of the reflux condensate is fed into an upper portion of the absorber, thereby further increasing the recovery of propane. While the ratios between the first and the second portion need not necessarily be fixed, typical ratios of first portion to second portion are generally between 0.5 and 2. However, alternative ratios between 2 and 3, and higher, and between 0.2 and 0.5 and lower are also contemplated. Thus, at least a portion of the reflux condensate can be employed to (a) increase the overall propane recovery and (b) reduce the energy cost for generating the condensate by extracting a cold reject vapor portion from the reflux condensate to generate the condensate. There are various condensers known in the art, an all of the known condensers are contemplated suitable for use herein. For example, contemplated propane recovery plant may employ a core type or plate and frame type condenser that is fluidly coupled to a deethanizer column (preferable integral overhead). In alternative aspects, the condenser may also employ a refrigerant that has been cooled by a turboexpander.

It should further be appreciated that the operating pressures between the deethanizer and the absorber are such that the deethanizer operates at a slightly higher pressure than the absorber. Consequently, it is contemplated that the flow from the second portion of the reflux condensate to the absorber does generally not require a pump or other equipment, which advantageously helps minimizing downtime due to maintenance of rotating parts.

In alternative aspects of the inventive subject matter, it is contemplated that the second column further comprises an integral water removal contactor, which preferably employs triethylene glycol as a dehydrating agent. There are various water removal contactors known in the art, and all of them are contemplated suitable for use herein. For example, a suitable water removal contactor comprises a structured packing or tray section. Where an integral water removal contactor is disposed within the second column, it is especially preferred that the water removal contactor is disposed between the level at which a wet liquid feed gas and the product fluid in gas form enter the second column. In another example, where the deethanizer receives a wet liquid feed gas and where the deethanizer has an integral water removal contactor, it is especially contemplated that at least a portion of the wet liquid feed gas is vaporized in the deethanizer column by a reboiler, and subsequently dried in the deethanizer column by contacting a triethylene glycol solution.

Wet liquid feed gas 186 is typically provided via gas separation element 180 that receives wet process gas 182. The gas separation element is preferably a vapor liquid separator that further produces a wet gaseous feed gas. It should be especially appreciated that the integration of the water removal contactor permits direct feeding of a wet liquid feed gas into the second column. The term "wet" as used herein means water containing, wherein the water is present at a concentration of at least 0.001 to 0.01 mol %.

Thus, in a particularly contemplated aspect of the inventive subject matter, a plant may include a feed gas separation element that receives a wet process gas, and that produces a wet gaseous feed gas and a wet liquid feed gas. A deethanizer column receives the wet liquid feed gas, wherein the deethanizer column comprises an integral water removal contactor, wherein the deethanizer column further comprises an integral overhead condenser that forms a reflux condensate, of which a first portion is recycled into the deethanizer column and of which a second portion is fed into an absorber column. It should be particularly appreciated that this configuration advantageously permits processing of both a wet liquid feed gas and a wet gaseous feed gas in a single process, whereas prior art processes require treatment of the wet liquid feed gas and the wet gaseous feed gas in two separate processes.

With respect to the feed gas separation element, it is preferred that the feed gas separation element comprises a vapor liquid separtor, however, alternative separation elements also include a centrifugal separator, a gravity separator, or a mechanical separator. Contemplated wet process gases particularly include light hydrocarbon vapor and hydrocarbon liquids and water. Consequently, the wet gaseous feed gas and the wet liquid feed gas include wet gaseous light hydrocarbons and wet liquid—heavy hydrocarbons and water. With respect to the deethanizer, the integral water removal contactor, the integral overhead condenser, and the reflux condensate the same considerations as described above apply.

In a still further aspect of the inventive subject matter, a method of improving the recovery of propane from a feed gas comprises one step in which an absorber column and a deethanizer column are provided, wherein the deethanizer column has an overhead condenser that utilizes at least part of a cold reject vapor from the absorber column as a refrigerant, and wherein the overhead condenser produces a reflux fluid. In a further step, a first recycling loop is formed in which a first portion of the reflux fluid is recycled into the deethanizer column, and in another step a second recycling loop is formed in which a second portion of the reflux fluid is fed into the absorber column. In yet another step, a third recycling loop is formed in which a product fluid from the absorber is heat exchanged to provide absorber feed gas cooling and fed into the deethanizer column. It should be appreciated that contemplated methods achieve recovery of propane from the absorber feed gas comprises recovering up to 99 mol % of propane from the feed gas, wherein the feed gas is typically a wet process gas.

Thus, specific embodiments and applications of high propane recovery have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A plant, comprising:
   an absorber column that receives an absorber feed gas, and that produces a cold reject vapor and a product fluid;
   a second column that receives at least part of the product fluid in a gas form, wherein the second column is further fluidly coupled to a condenser that forms a reflux condensate by using at least part of the cold reject vapor as a refrigerant; and
   wherein a first portion of the reflux condensate is recycled into the second column and wherein a second portion of the reflux condensate is fed into the absorber column.

2. The plant according to claim 1 wherein the second column comprises a deethanizer column.

3. The plant according to claim 2 wherein the condenser is an integral overhead condenser.

4. The plant according to claim 2 wherein the condenser employs propane as a refrigerant.

5. The plant according to claim 2 wherein the second column further comprises an integral water removal contactor.

6. The plant according to claim 5 wherein the deethanizer column further receives a wet liquid feed gas.

7. The plant according to claim 5 wherein the integral water removal contactor utilizes triethylene glycol as a dehydrating agent.

8. The plant according to claim 2 wherein the second column further produces a purified product fluid.

9. The plant according to claim 8 wherein the purified product fluid predominantly comprises propane and higher hydrocarbons.

10. The plant according to claim 1 wherein the condenser further receives refrigerant from a turboexpander.

11. The plant according to claim 1 wherein the condenser employs at least in part propane as a refrigerant.

12. The plant according to claim 2 wherein the absorber column is fabricated from stainless steel and the deethanizer column is fabricated from low temperature carbon steel.

13. A plant, comprising:
    a feed gas separation element that receives a wet process gas, and that produces a wet gaseous feed gas and a wet liquid feed gas;

a deethanizer column that receives the wet liquid feed gas, wherein the deethanizer column comprises an integral water removal contactor; and wherein the deethanizer column further comprises an integral overhead condenser that forms a reflux condensate, of which a first portion is recycled into the deethanizer column and of which a second portion is fed into an absorber column.

14. The plant according to claim 13 wherein the feed gas separation element comprises vapor liquid separator.

15. The plant according to claim 13 wherein at least a portion of the wet liquid feed gas is vaporized in the deethanizer column by a reboiler.

16. The plant according to claim 15 wherein at least a portion of the vaporized wet liquid feed gas is dried in the deethanizer column by contacting a triethylene glycol solution.

17. A method of improving the recovery of propane from a feed gas, comprising:

providing an absorber column, and a deethanizer column with an overhead condenser that utilizes at least part of a cold reject vapor from the absorber column as a refrigerant, and wherein the overhead condenser produces a reflux fluid;

forming a first recycling loop in which a first portion of the reflux fluid is recycled into the deethanizer column;

forming a second recycling loop in which a second portion of the reflux fluid is fed into the absorber column; and forming a third recycling loop in which a product fluid from the absorber is heat exchanged to provide absorber feed gas cooling and fed into the deethanizer column.

18. The method according to claim 17 wherein the deethanizer further comprises an integral water removal contactor.

19. The method according to claim 17 wherein the condenser further employs a propane refrigerant.

20. The method of claim 17 wherein the recovery of propane from a feed gas comprises recovering up to 99 mol % of propane from the feed gas.

* * * * *